(12) United States Patent
Kanai et al.

(10) Patent No.: US 8,512,248 B2
(45) Date of Patent: Aug. 20, 2013

(54) ULTRASONOGRAPH THAT MEASURES TISSUE DISPLACEMENTS BASED ON A REFERENCE POINT

(75) Inventors: Hiroshi Kanai, Miyagi (JP); Hideyuki Hasegawa, Miyagi (JP); Takao Suzuki, Kanagawa (JP)

(73) Assignees: Tohoku University, Miyagi (JP); Panasonic Corporation, Osaka (JP)

( * ) Notice: Subject to any disclaimer, the term of this patent is extended or adjusted under 35 U.S.C. 154(b) by 592 days.

(21) Appl. No.: 12/442,445

(22) PCT Filed: Sep. 25, 2007

(86) PCT No.: PCT/JP2007/068513
§ 371 (c)(1),
(2), (4) Date: Jun. 10, 2009

(87) PCT Pub. No.: WO2008/038615
PCT Pub. Date: Apr. 3, 2008

(65) Prior Publication Data
US 2010/0016721 A1    Jan. 21, 2010

(30) Foreign Application Priority Data
Sep. 25, 2006    (JP) ................... 2006-259123

(51) Int. Cl.
*A61B 8/00*    (2006.01)
(52) U.S. Cl.
USPC .......................................... 600/437; 600/449
(58) Field of Classification Search
USPC ....................................................... 600/437
See application file for complete search history.

(56) References Cited

U.S. PATENT DOCUMENTS

| | | | |
|---|---|---|---|
| 4,630,612 A | * | 12/1986 | Uchida et al. ................. 600/441 |
| 5,280,787 A | * | 1/1994 | Wilson et al. ................. 600/456 |
| 5,840,028 A | | 11/1998 | Chubachi et al. |

(Continued)

FOREIGN PATENT DOCUMENTS

| | | |
|---|---|---|
| JP | 62-266040 | 11/1987 |
| JP | 10-5226 | 1/1998 |

(Continued)

OTHER PUBLICATIONS

International Search Report for corresponding Application No. PCT/JP2007/068513 mailed Dec. 18, 2007.

(Continued)

*Primary Examiner* — Long V. Le
*Assistant Examiner* — Bradley Impink
(74) *Attorney, Agent, or Firm* — Renner, Otto, Boisselle & Sklar, LLP

(57) ABSTRACT

An ultrasonic diagnostic apparatus includes: a transmitting section for driving an ultrasonic probe that sends out an ultrasonic transmitted wave toward a vital tissue; a receiving section for amplifying an ultrasonic reflected wave, produced by getting the ultrasonic transmitted wave reflected by the vital tissue and then received at the ultrasonic probe, to generate a received signal; a reference point shift measuring section for measuring the magnitude of shift of a reference point that has been set on the received signal; a received signal adjusting section for adjusting the position of the received signal in a distance direction according to the magnitude of shift of the reference point; and a shape variation calculating section for determining the magnitudes of positional displacements at multiple measuring points that have been set in the vital tissue by the received signal adjusted.

13 Claims, 12 Drawing Sheets

(56) References Cited

U.S. PATENT DOCUMENTS

| | | | |
|---|---|---|---|
| 5,938,606 A * | 8/1999 | Bonnefous | 600/437 |
| 6,267,728 B1 * | 7/2001 | Hayden | 600/481 |
| 6,728,394 B1 | 4/2004 | Chen et al. | |
| 2004/0260180 A1 * | 12/2004 | Kanai et al. | 600/449 |
| 2005/0240101 A1 * | 10/2005 | Kato et al. | 600/437 |
| 2006/0004288 A1 * | 1/2006 | Kato et al. | 600/443 |
| 2006/0065056 A1 | 3/2006 | Zheng et al. | |
| 2007/0055149 A1 * | 3/2007 | Suzuki et al. | 600/437 |
| 2007/0219447 A1 * | 9/2007 | Kanai et al. | 600/450 |
| 2008/0125651 A1 * | 5/2008 | Watanabe et al. | 600/437 |
| 2009/0012399 A1 * | 1/2009 | Sunagawa et al. | 600/454 |

FOREIGN PATENT DOCUMENTS

| | | |
|---|---|---|
| JP | 10-127630 | 5/1998 |
| JP | 2000-229078 | 8/2000 |
| WO | WO 2006082966 A1 * | 8/2006 |

OTHER PUBLICATIONS

Hiroshi Kanai et al., "Elasticity Imaging of Atheroma With Transcutaneous Ultrasound Preliminary Study", Circulation, vol. 107, pp. 3018-3021, 2003.

* cited by examiner

STEPS 200~206

STEP 207

ULTRASONOGRAPH THAT MEASURES TISSUE DISPLACEMENTS BASED ON A REFERENCE POINT

TECHNICAL FIELD

The present invention relates to an ultrasonic diagnostic apparatus. More particularly, the present invention relates to an ultrasonic diagnostic apparatus for inspecting the characteristic of a vital tissue.

BACKGROUND ART

Recently, the number of people suffering from various cardiovascular system diseases, including heart infarction and brain infarction, has been on the rise, thus making it more and more urgent to prevent and treat these diseases.

The onset of heart or brain infarction is closely correlated to atherosclerosis. More specifically, if an atheroma is created on the arterial wall or if no arterial cells are produced anymore due to various factors such as elevated blood pressure, then the artery loses its elasticity to become hard and fragile. Also, if the blood vessel is clogged up where the atheroma has been created or if a vascular tissue covering the atheroma has ruptured, then the atheroma will move itself into the blood vessel to clog up the artery elsewhere or to rupture the hardened portions of the artery. As a result, these diseases are caused. That is why it is important to diagnose the atherosclerosis as early as possible to prevent or treat these diseases.

In the prior art, the lesion of atherosclerosis is diagnosed by directly observing the inside of the blood vessel with a vascular catheter. However, this diagnosis needs to be carried out with a vascular catheter inserted into the blood vessel of a patient, thus imposing a heavy load on him or her. For that reason, the vascular catheter observation is usually adopted to locate the lesion of atherosclerosis in a patient who is already known to suffer from that disease but has never been used to make a medical checkup on a supposedly healthy person.

A checkup may be easily made without imposing excessively heavy load on a patient if the index of cholesterol, which is one of major causes of atherosclerosis, or the blood pressure is measured. However, none of these values directly indicates the degree of advancement of atherosclerosis.

Also, if the atherosclerosis can be diagnosed early enough to administer a dedicated curative medicine to its patient, then the disease can be treated effectively. However, it is said that once the atherosclerosis has advanced to a certain degree, the farther advancement of that disease can be checked with the administration of curative medicine but it is difficult to repair the hardened artery completely.

For these reasons, a method or apparatus for diagnosing the atherosclerosis at an early stage of its advancement without imposing too much load on its patient is now in high demand.

Meanwhile, an ultrasonic diagnostic apparatus or an X-ray diagnostic apparatus has been used in the prior art as a non-invasive medical apparatus that imposes only a light load on a person under test. Specifically, by irradiating the testee with an ultrasonic wave or an x-ray that has been produced externally, shape information or information about the variation in the shape of his or her internal body with time can be acquired without causing too much pain to him or her. When the information about the variation with time (i.e., mobility information) in the shape of an object under test in his or her body can be obtained, the characteristic information of the object can be obtained. That is to say, the vascular elastic property of the organism can be known and the degree of advancement of the atherosclerosis can be detected directly.

Among other things, the ultrasonic diagnosis is superior to the X-ray diagnosis because the ultrasonic diagnosis can be made just by putting an ultrasonic probe on a person under test. That is to say, in the ultrasonic diagnosis, there is no need to administer a contrast medium to the person under test and there is no concern about potential X-ray exposure, either.

Besides, some ultrasonic diagnostic apparatuses can recently have significantly improved measuring accuracy thanks to remarkable advancement of electronic technologies. As a result, ultrasonic diagnostic apparatuses for measuring the very small movement of a vital tissue have been developed. For example, according to the technique disclosed in Patent Document No. 1, vibration components of a vascular movement, having an amplitude of several micrometers and a frequency of as high as several hundreds of Hz, can be measured accurately. Thus, it was reported that the thickness variation or strain of the vascular wall could be measured highly accurately on the order of several micrometers.

By adopting such a high-accuracy measuring technique, the two-dimensional distribution of the elastic properties of the arterial wall can be plotted in detail. For example, Non-Patent Document No. 1 shows an example of presenting the two-dimensional distribution of the moduli of elasticity of the carotid arterial wall as an image superimposed on a B-mode tomogram. The hardness of the arterial wall is not uniform but has some distribution. That is why in diagnosing the atherosclerosis, it is important to understand properly the local distribution of the moduli of elasticity, which are characteristic quantities indicating the degree of advancement of the atherosclerosis.

Patent Document No. 1: Japanese Patent Application Laid-Open Publication No. 10-5226

Non-Patent Document No. 1: Hiroshi Kanai et al., "Elasticity Imaging of Atheroma with Transcutaneous Ultrasound Preliminary Study", Circulation, Vol. 107, pp. 3018-3021, 2003

DISCLOSURE OF INVENTION

Problems to be Solved by the Invention

If the modulus of elasticity of an arterial vascular wall is determined by such a method, the magnitude of strain of the arterial vascular wall needs to be obtained by measuring. That is to say, the magnitude of strain is calculated as the difference between the magnitudes of displacements at two measuring points that have been set on the vascular wall.

Meanwhile, the arterial vascular wall repeatedly dilates and contracts as blood is pumped out of the heart. In that case, the overall vascular wall is displaced in the radial direction while being strained. The present inventors discovered via experiments that the overall vascular wall was displaced in the radial direction by a magnitude that was about ten times as great as that of the strain of the vascular wall itself. The error of measurement of the magnitude of displacement is proportional to the magnitude of displacement itself. That is why according to the method disclosed in Patent Document No. 1 or Non-Patent Document No. 1, the errors to be caused by the radial displacement of the overall vascular wall will accumulate when the magnitude of strain of the arterial vascular wall is determined. Consequently, it is difficult to calculate the modulus of elasticity accurately.

In order to overcome the problems described above, the present invention has an object of providing an ultrasonic diagnostic apparatus that can carry out measurements highly accurately with the decrease in measuring accuracy due to those factors minimized.

Means for Solving the Problems

An ultrasonic diagnostic apparatus according to the present invention includes: a transmitting section for driving an ultrasonic probe that sends out an ultrasonic transmitted wave toward a vital tissue; a receiving section for amplifying an ultrasonic reflected wave, produced by getting the ultrasonic transmitted wave reflected by the vital tissue and then received at the ultrasonic probe, to generate a received signal; a reference point shift measuring section for measuring the magnitude of shift of a reference point that has been set on the received signal; a received signal adjusting section for adjusting the position of the received signal in a distance direction according to the magnitude of shift of the reference point; and a shape variation calculating section for determining the magnitudes of positional displacements at multiple measuring points that have been set in the vital tissue by the adjusted received signal.

In one preferred embodiment, the vital tissue makes a movement in a cycle time corresponding to one cardiac cycle, and the reference point shift measuring section determines the magnitude of the greatest shift of the reference point within one cardiac cycle.

In this particular preferred embodiment, the transmitting section and the receiving section send and receive the ultrasonic transmitted waves a number of times every cardiac cycle so as to scan a measuring region that has been defined in the vital tissue, thereby generating received signals for multiple frames. The received signal adjusting section adjusts the position of the received signal in the distance direction at least in a frame in which the reference point has the greatest magnitude of shift in each said cardiac cycle.

In a specific preferred embodiment, the received signal adjusting section adjusts the position of the received signal in the distance direction in the frame in which the reference point has the greatest magnitude of shift such that the positions of the reference point are aligned with each other in the distance direction.

In another preferred embodiment, the transmitting section and the receiving section send and receive the ultrasonic transmitted waves a number of times every cardiac cycle so as to scan a measuring region that has been defined in the vital tissue, thereby generating received signals for multiple frames. The reference point shift measuring section measures the magnitude of shift of the reference point every frame. If the magnitude of shift is at least an integral number of times (but not zero times) as much as a predetermined value, then the reference point shift measuring section multiplies the predetermined value by the integer and outputs the product as the magnitude of shift to the received signal adjusting section, which adjusts the position of the received signal in the distance direction according to the magnitude of shift.

In this particular preferred embodiment, the received signal adjusting section adjusts the position of the received signal in the distance direction so as to cancel the magnitude of shift.

In a specific preferred embodiment, the predetermined value is equal to a sampling interval.

In still another preferred embodiment, the vital tissue is an arterial vascular wall, and the reference point is set at a point on the received signal that corresponds to the boundary between a vascular lumen and an intima.

In yet another preferred embodiment, the vital tissue makes a movement in a cycle time corresponding to one cardiac cycle, and the shape variation calculating section calculates the greatest thickness difference between two arbitrary points that have been set based on the multiple measuring points according to the magnitudes of positional displacements.

In this particular preferred embodiment, the ultrasonic diagnostic apparatus further includes a tissue characteristic value calculating section for calculating a characteristic property value of the tissue based on the greatest thickness difference.

In a specific preferred embodiment, the vital tissue is an artery and the characteristic property value is a modulus of elasticity.

In yet another preferred embodiment, the reference point shift measuring section determines the magnitude of shift by analyzing the phase at the reference point of the received signal.

In yet another preferred embodiment, the shape variation calculating section calculates the magnitudes of positional displacements by analyzing the phases at the respective measuring points of the adjusted received signal.

Effects of the Invention

According to the present invention, a reference point is set on a received signal and the magnitude of shift of the reference point is measured, thereby determining the magnitude of displacement of the overall vital tissue, which is the object of measurement. And based on this magnitude of displacement, the received signal is shifted in the distance direction, thereby canceling the displacement of the overall vital tissue. That is why by measuring a tiny movement of the vital tissue using such a shifted signal, the error that would have grown proportionally to the magnitude of shift can be minimized and the magnitude of such a small displacement, the variation in thickness, the magnitude of strain or the modulus of elasticity of the vital tissue can be measured with high accuracy.

Figure 1A:
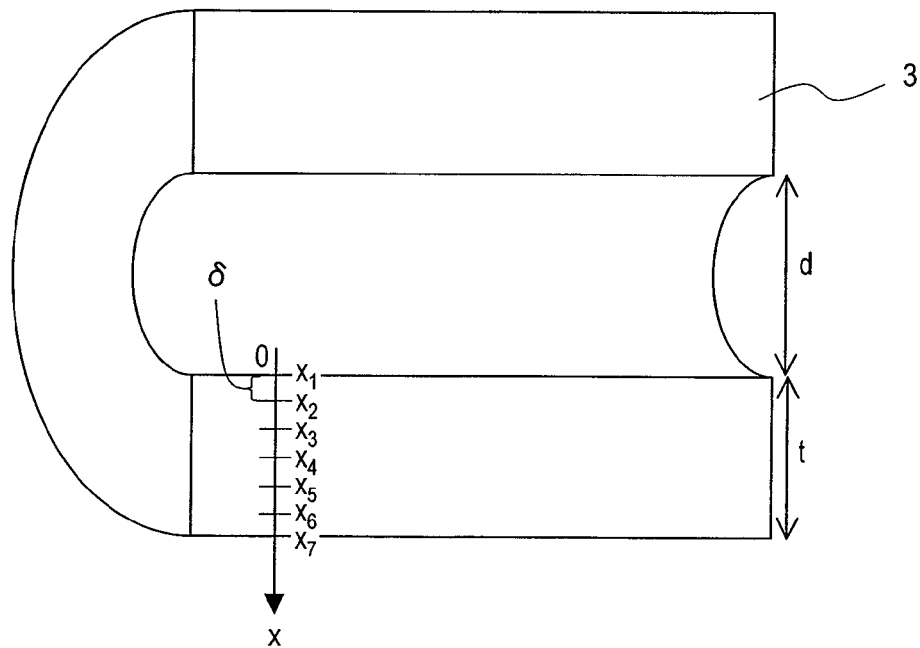
FIG. 1A schematically illustrates a cross section of a contracted artery.

DESCRIPTION OF REFERENCE NUMERALS 1 extravascular tissue
2 body surface
3 blood vessel
4 vascular anterior wall
5 blood
11 ultrasonic diagnostic apparatus
12 blood pressure manometer
13 ultrasonic probe
14 transmitting section
15 receiving section
16 time delay control section
19 computing section
20 computed data storage section
21 display section
22 electrocardiograph
51 reference point setting section
52, 56 reference point shift measuring section
53, 57 received signal adjusting section
54, 58 shape variation calculating section
55 tissue characteristic value calculating section

BEST MODE FOR CARRYING OUT THE INVENTION

An ultrasonic diagnostic apparatus according to the present invention calculates the magnitude of displacement and the greatest thickness difference, which are shape measured values of respective portions of a vital tissue as the object of measurement, and also calculates the magnitude of strain, the modulus of elasticity, and the coefficient of viscosity thereof, which are characteristic property values. As will be described later, in a situation where respective portions of a tissue make tiny displacements while the overall tissue is being displaced or moving, the present invention can be used particularly effectively to measure the magnitudes of those tiny displacements of the respective portions.

Figure 1B:
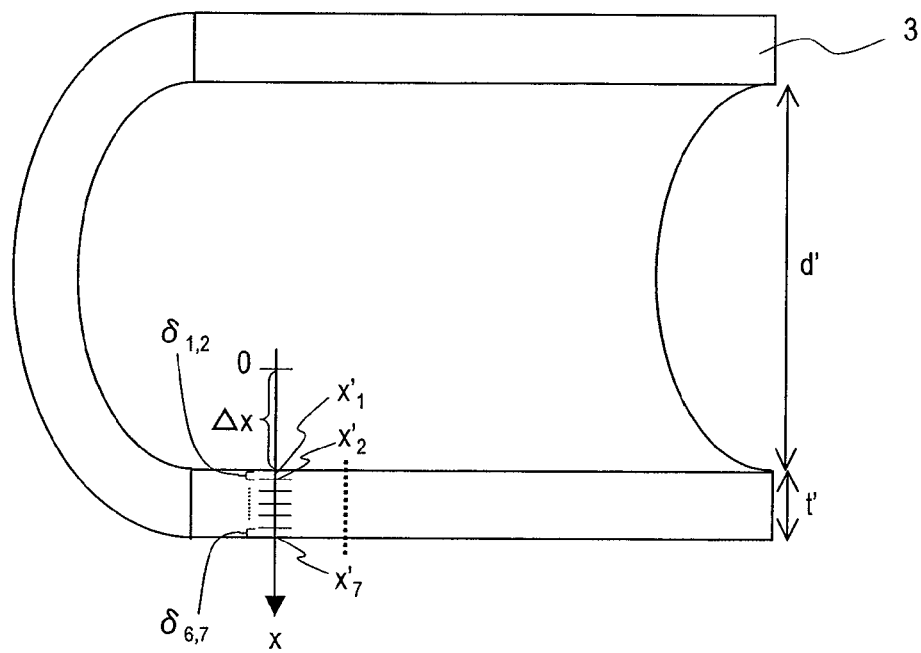
FIG. 1B schematically illustrates a cross section of a dilated artery.

FIGS. 1A and 1B schematically illustrate a cross section of the artery 3 of an organism as viewed on a plane that is parallel to the axial direction thereof. Specifically, FIGS. 1A and 1B illustrate a contracted state and a dilated state of the blood vessel. As shown in FIG. 1A, in a situation where the artery 3 is contracted, the vascular lumen of the artery 3 is supposed to have a diameter d and the vascular wall thereof is supposed to have a thickness t. Supposing the boundary between the vascular wall and the vascular lumen is the origin, coordinates are put in the radial direction. More specifically, measuring points x1 and x7 are set on the boundary between the vascular wall and the vascular lumen and on the boundary between the vascular wall and the extravascular tissue, respectively, and the other measuring points x2 through x6 are set by equally dividing the interval between x1 and x7 into six. The interval between each adjacent pair of the measuring points x1 through x7 is supposed to be $\delta$.

As shown in FIG. 1B, when blood is pumped out due to the ejection from the heart, the vascular wall of the artery 3 comes to have a dilated vascular lumen and a reduced thickness. That is to say, the dilated vascular lumen d' and the thickness t' of the dilated vascular wall satisfy d'>d and t'<t, respectively.

In this case, suppose the measuring points x1 through x7 that have been set on the vascular wall have moved to x1' through x7', respectively, with the boundary between the vascular wall and the vascular lumen of the contracted blood vessel fixed at the origin. As can be easily from FIG. 1B, as the vascular wall dilates, the overall vascular wall moves in the radial direction. In addition, as the vascular wall comes to have a reduced thickness, respective portions of the vascular wall tissue are strained, or have been compressed, so to speak. In this case, not all of these portions have been strained uniformly. If the distance between each adjacent pair of the measuring points x1' through x7' is identified by $\delta_{1,2}$ through $\delta_{6,7}$, then the magnitude of the strain of the tissue between the measuring points x1' and x2' is calculated by $(\delta_{1,2}-\delta)/\delta$. And the modulus of elasticity can be obtained based on the magnitude of strain.

As disclosed in Patent Document No. 1, the magnitude of strain of a vascular wall tissue can be determined by detecting the position of each displaced measuring point with the phase difference of the received signal traced at that measuring point and by calculating the maximum and minimum values of positional differences between each pair of the measuring points.

According to the method of Patent Document No. 1, the positions of the respective displaced measuring points are determined first. That is why if the magnitude of displacement of each measuring point is great, then the position of each displaced measuring point will have a significant error proportionally to the magnitude of displacement. As a result, the modulus of elasticity also has an error that is proportional to the magnitude of displacement of each measuring point for the following reasons.

Specifically, to calculate the magnitude of displacement of an object based on the phase of the received signal as in the method disclosed in Patent Document No. 1, information about the center frequency of ultrasonic waves is required. If multiple objects that will scatter the ultrasonic waves are present within the measuring region, those scattered waves will interfere with each other. The ultrasonic waves used for measuring purposes are applied as pulses, which do not have a single frequency but a finite frequency band. That is why if a dip has been produced in the vicinity of the real center frequency f0 due to the interference, then the center frequency will change apparently. And if the center frequency of the received wave is different from f0, the error produced will be proportional to the magnitude of displacement of the object.

As for the arterial vascular wall, the magnitude of strain of the arterial wall due to the heartbeat is just one tenth or less of the magnitude of positional displacement (i.e., translation) of the overall arterial wall. That is why the error to be caused in the positional displacement component becomes far greater than the one to be caused in the magnitude of strain that should be measured. For example, if the center frequency changes 10%, the error caused in the positional displacement component becomes approximately equal to the magnitude of strain itself. As a result, the magnitude of strain cannot be measured accurately.

However, the measured value that is needed in calculating the modulus of elasticity is the exact magnitude of strain between two points, not the exact position of each measuring point. That is why if a reference point is set and if the magnitude of relative displacement of a measuring point with respect to the reference point is measured, then the magnitude of positional displacement of each measuring point can be decreased and the error to be proportional to the magnitude of displacement can be reduced.

As for the arterial vascular wall, the echo from the lumen-intima boundary is preferably used as a reference. This is because the sounding echo from the lumen-intima boundary is hardly affected by interference and has a little variation in center frequency.

For example, in a situation where the boundary between the vascular wall of the dilated artery and the vascular lumen has been displaced by Δx as shown in FIG. 1B, even if the received signal is adjusted as if x1' was never displaced, the magnitudes of relative displacements of the other measuring points x2' through x7' with respect to x1' can still be calculated. As a result, the magnitude of displacement of each measuring point can be reduced by Δx. That is why by canceling the displacement component of the vascular wall before the phase change starts to be calculated, the error to be proportional to the magnitude of displacement can be reduced. By adopting this method, the present invention realizes an ultrasonic diagnostic apparatus that can carry out measurements with high accuracy.

Embodiment 1

Hereinafter, a first preferred embodiment of an ultrasonic diagnostic apparatus according to the present invention will be described. This first preferred embodiment contributes to calculating the magnitude of maximum strain of each measuring point within one cardiac cycle with high accuracy and can be used particularly effectively to measure the modulus of elasticity.

Figure 2:
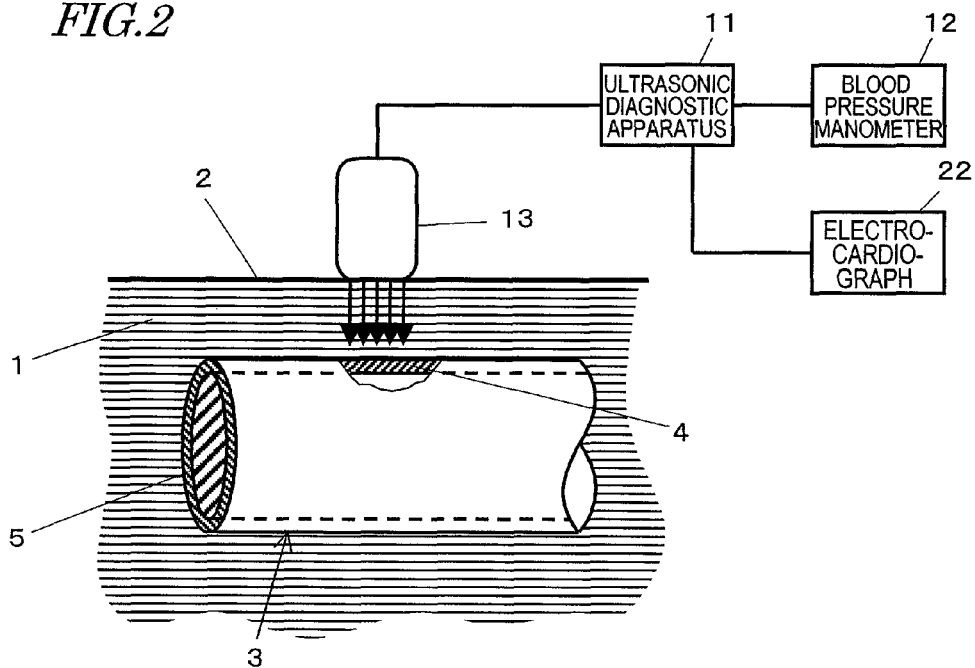
FIG. 2 is a block diagram illustrating an arrangement for a situation where the ultrasonic diagnostic apparatus of the present invention is used to inspect the tissue and characteristic of a vascular wall.

FIG. 2 is a block diagram showing an arrangement for a situation where the ultrasonic diagnostic apparatus 11 of this preferred embodiment is used to inspect the tissue and characteristic of a vascular wall. An ultrasonic probe 13, connected to the ultrasonic diagnostic apparatus 11, is held in close contact with the body surface 2 of a person under test and transmits an ultrasonic wave into a vital tissue inside an extravascular tissue 1. The transmitted ultrasonic wave is reflected by a blood vessel 3 and blood 5, scattered, and only a portion of it comes back to, and is received as an echo (i.e., the ultrasonic reflected wave) by, the ultrasonic probe 13. The ultrasonic diagnostic apparatus 11 performs analysis and computations on the received signal, thereby acquiring the shape information of the vascular anterior wall 4 and the vascular posterior wall. In accordance with the method disclosed in Patent Document No. 1, for example, the ultrasonic diagnostic apparatus 11 determines the instantaneous position of the object by a restricted minimum square method using both the amplitude and phase of a detection signal, thereby performing phase tracking highly precisely (where the magnitude of positional displacement has a measuring accuracy of about ±0.2 μm) and measuring variations in the position and thickness of a very small spot on the vascular anterior wall 4 with time with sufficient precision. A blood pressure manometer 12 is preferably connected to the ultrasonic diagnostic apparatus 11. By using the blood pressure data obtained with the blood pressure manometer 12, the ultrasonic diagnostic apparatus 11 can also estimate the modulus of elasticity of a very small spot on the vascular anterior wall 4. An electrocardiograph 22 is preferably further connected to the ultrasonic diagnostic apparatus 11, which receives an electrocardiogram from the electrocardiograph 22 and uses it as a trigger signal that determines the timings of data acquisition and data resetting. The electrocardiograph 22 may be replaced with any other biomedical signal detecting means such as a phonocardiograph or a sphygmograph. In that case, a phonocardiogram or a sphygmogram may be used as a trigger signal instead of the electrocardiogram.

Figure 3:
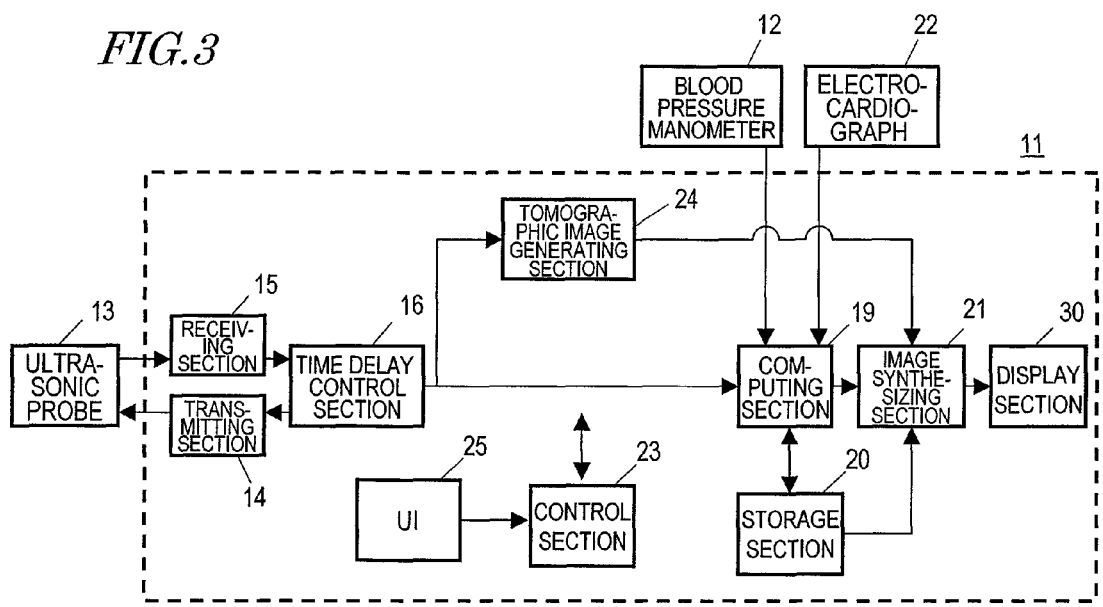
FIG. 3 is a block diagram illustrating a configuration for an ultrasonic diagnostic apparatus as a first preferred embodiment of the present invention.

Hereinafter, the configuration and operation of the ultrasonic diagnostic apparatus 11 will be described in further detail. FIG. 3 is a block diagram illustrating a configuration for the ultrasonic diagnostic apparatus 11, which includes a transmitting section 14, a receiving section 15, a time delay control section 16, a computing section 19, a computed data storage section 20, an image synthesizing section 21 and a display section 30. The ultrasonic diagnostic apparatus 11 further includes a control section 23 for performing an overall control on all of these sections. Using a user interface 25 such as a mouse, a keyboard or a trackball, the operator can instruct the control section 23 how to operate the ultrasonic diagnostic apparatus 11.

The transmitting section 14 generates a predetermined drive pulse signal and outputs it to the ultrasonic probe 13. An ultrasonic transmitted wave, transmitted by the ultrasonic probe 13 in response to the drive pulse signal, is reflected and scattered by a vital tissue such as the blood vessel 3 to produce an ultrasonic reflected wave, which is then received at the ultrasonic probe 13. The interval of application of the drive pulses that generate the ultrasonic waves is determined with the depth of the object of measurement and the velocity of the ultrasonic wave into consideration such that no ultrasonic pulses, adjacent to each other on the time axis, overlap with each other.

The receiving section 15 receives the ultrasonic reflected wave through the ultrasonic probe 13. The receiving section 15 includes an A/D converting section and amplifies the ultrasonic reflected wave, thereby generating a received signal. And then the receiving section 15 further converts the received signal into a digital signal. The transmitting section 14 and receiving section 15 may be made of electronic components, for example.

The time delay control section 16 is connected to the transmitting section 14 and receiving section 15 in order to control the time delay of the drive pulse signal to be supplied from the transmitting section 14 to a group of ultrasonic vibrators in the ultrasonic probe 13. In this manner, an ultrasonic beam of the ultrasonic transmitted wave to be transmitted from the ultrasonic probe 13 can have its acoustic line directions and depths of focus changed. Furthermore, by controlling the time delay of the received signal that has been received by the ultrasonic probe 13 and then amplified by the receiving section 15, the aperture sizes and depths of focus can also be changed. The output of the time delay control section 16 is passed to the computing section 19 and a tomographic image generating section 24.

The transmitting section 14 and the receiving section 15 send and receive ultrasonic transmitted waves a number of times in every cardiac cycle so as to scan a measuring region that has been defined in the vital tissue, thereby generating received signals for multiple frames per cardiac cycle.

The tomographic image generating section 24 generates a tomographic image based on the received signal. For example, the tomographic image generating section 24 converts the amplitude and intensity of the received signal into information representing the luminance of an image to be presented on the display section 30, thereby generating a B-mode image.

Figure 4:
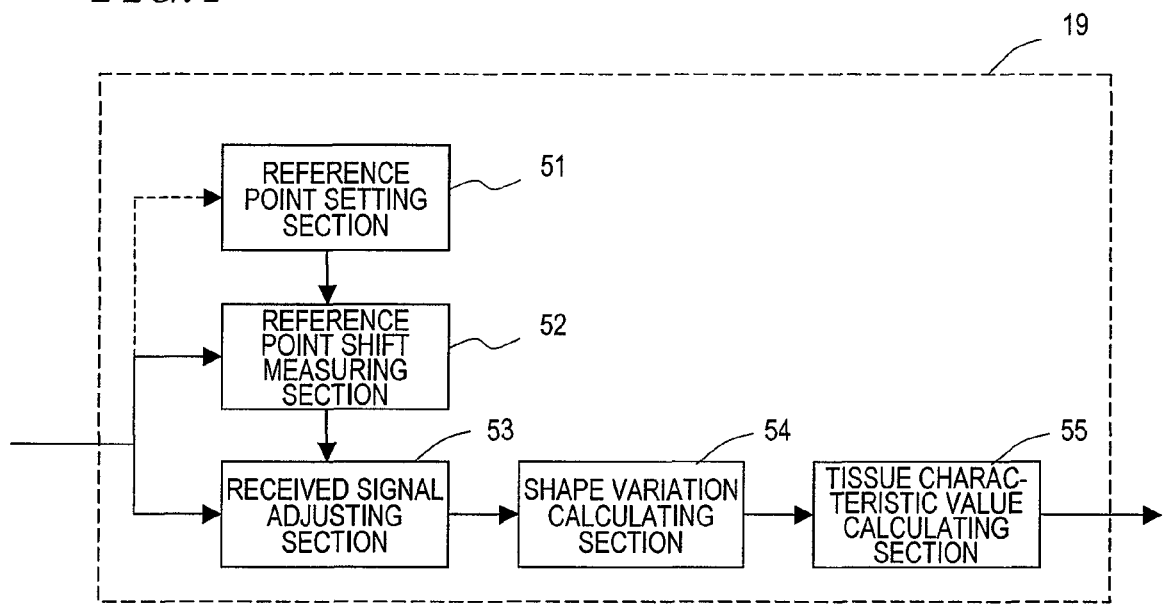
FIG. 4 is a block diagram illustrating a detailed configuration for the computing section of the ultrasonic diagnostic apparatus shown in FIG. 2.

FIG. 4 is a block diagram illustrating a detailed configuration for the computing section 19, which includes a reference point setting section 51, a reference point shift measuring section 52, a received signal adjusting section 53, a shape variation calculating section 54 and a tissue characteristic value calculating section 55. The computing section 19 may be implemented as either a software program or as hardware components.

The reference point setting section 51 sets a reference point on the axis of the received signal, which runs in the distance direction, in order to determine the magnitude of displacement of the overall vital tissue that is the object of measurement. The reference point is preferably set at a point on the received signal, where the amplitude is great enough to avoid being affected by speckle or any other kind of noise easily.

When the ultrasonic diagnostic apparatus carries out measurements, the respective portions of the vital tissue are located at mutually different depths as measured from the surface of the ultrasonic probe 13. That is why the ultrasonic reflected waves that have come from those portions of the vital tissue have time delays that have varying lengths according to their location in the depth direction. For that reason, the axis of the received signal in the distance direction corresponds to the distribution of the vital tissue.

Since the vascular wall of the artery is the object of measurement according to this preferred embodiment, the reference point is preferably set on the axis of the received signal in the distance direction, which is associated with the boundary between the blood flow running through the vascular lumen and the intima, for example. This is because the acoustic impedance changes so significantly between the blood flow and the intima that an ultrasonic wave with relatively large amplitude is reflected from their boundary and is hardly affected by speckle noise.

The reference point on the boundary between the blood flow and the intima may be set either manually or automatically. If the reference point is set manually, the operator needs to specify the boundary between the blood flow and the intima by moving a cursor, for example, on a B-mode tomographic image being presented on the display section 30. Then, the reference point setting section 51 determines the point on the received signal based on the cursor location information. On the other hand, if the reference point is set automatically, the reference point setting section 51 sets the reference point based on the amplitude or any other appropriate parameter of the received signal. The ultrasonic waves are reflected or scattered less from the blood flow than from inside of the vascular wall. That is why even if the boundary between the blood flow and the intima is defined automatically based on the amplitude, for example, the reference point can still be set relatively accurately.

The reference point shift measuring section 52 measures the magnitude of shift of the reference point that has been set. According to this preferred embodiment, to calculate the modulus of elasticity of the vital tissue, among other things, the magnitude of maximum shift of the reference point is determined every cardiac cycle. Specifically, by analyzing the phase of the received signal at the reference point by the phase difference tracking technique disclosed in Patent Document No. 1, for example, the magnitude of shift of the reference point on the received signal for each frame is measured on a frame-by-frame basis, thereby determining the magnitude of maximum shift. The magnitude of shift of the reference point, which has been set by reference to the level of the received signal at a point in time when the artery contracted most significantly, is preferably measured.

The received signal adjusting section 53 receives the magnitude of maximum shift of the reference point, which has just been measured by the reference point shift measuring section 52, and adjusts the position in the distance direction of the received signal that has produced the greatest shift. Specifically, the received signal adjusting section 53 generates a signal by shifting the received signal in the distance direction by the magnitude of maximum shift of the reference point such that the shift of the reference point thus obtained goes zero. In this preferred embodiment, the reference point shift measuring section 52 determines the magnitude of maximum shift of the reference point every cardiac cycle. Also, according to this preferred embodiment, at least the received signal for that frame, in which the reference point had the greatest shift, needs to be adjusted to calculate the modulus of elasticity.

The shape variation calculating section 54 calculates the magnitudes of maximum relative shifts of the multiple measuring points that have been set in the vital tissue based on the adjusted received signal. This calculation can be done by the phase difference tracking method disclosed in Patent Document No. 1. Specifically, by analyzing the phases of the received signal at respective measuring points with the phase difference tracking method applied between the received signal at a point in time when the artery contracted most and the adjusted received signal, the magnitudes of maximum relative shifts of the respective measuring point are obtained. Furthermore, based on the magnitudes of the maximum relative shifts of those measuring points, the shape variation calculating section 54 also calculates the greatest thickness difference between two arbitrary points that have been set based on the multiple measuring points.

The tissue characteristic value calculating section 55 figures out the characteristic property value of the tissue based on the greatest thickness difference. In calculating an elastic property value, the tissue characteristic value calculating section 55 gets information about the highest and lowest blood pressures within one cardiac cycle from the blood pressure manometer 12 and calculates the modulus of elasticity based on the greatest thickness difference and the information about the blood pressures. If the measuring points are arranged two-dimensionally within the measuring region, the modulus of elasticity may be calculated between each pair of the measuring points. Then, the two-dimensional distribution of moduli of elasticity within the measuring region can be obtained.

The image synthesizing section 21 synthesizes together the tomographic image that has been generated by the tomographic image generating section 24 and the two-dimensional map data of the tissue's characteristic properties such as the moduli of elasticity that has been obtained by the computing section 19, and gets the resultant synthetic image presented on the display section 30.

Optionally, a storage section 20 may be provided for the ultrasonic diagnostic apparatus 11 such that the digitized received signal and/or the data that has been computed by the computing section 19 may be stored in the storage section 20. In that case, when the measuring process gets done, calculations may be carried out again with the positions of the reference point changed or the data stored in the storage section 20 may be presented on the display section 30.

As described above, the reference point shift measuring section 52 and the shape variation calculating section 54 preferably use the phase difference tracking method to calculate the magnitudes of shifts of the reference point and the respective measuring points. According to the phase difference tracking method, under the restriction that the amplitude does not change, but only the phase and reflection spot change, between two received signals measured at a very short time interval, the phase difference is calculated by a minimum square method so as to minimize the waveform mismatch between the two received signals as disclosed in detail in Patent Document No. 1. The motion velocity of the measuring point is derived from this phase difference and then integrated, thereby obtaining the magnitude of positional displacement. For that purpose, the reference point shift measuring section 52 and the shape variation calculating section 54 subject the received signal, of which the time delay has been controlled by the time delay control section 16, to a quadrature detection, thereby splitting the signal into a real part signal and an imaginary part signal. These sections 52 and 54 also filter out RF components, the components that have not been reflected by the object of measurement and other noise components from the real part and imaginary part signals that have been split. In this manner, the reference point shift measuring section 52 and the shape variation calculating section 54 get the computations done by the phase difference tracking method using the received signal processed. These sections 52 and 54 may be implemented as either a software program or hardware components.

In this case, the received signal to be shifted by the received signal adjusting section 53 may be either yet to be subjected, or has already been subjected, to the quadrature detection. If the received signal that has been subjected to the quadrature detection is used, however, the received signal needs to not only be shifted in the distance direction but also have its phase rotated according to the magnitude of shift. By calculating the greatest thickness difference $\Delta h$ between two points on a vital tissue in one cardiac cycle, the magnitude of strain S of the tissue is given by $S=\Delta h/H$, where H is the maximum thickness between those two points. On the other hand, the modulus of elasticity $\chi$ is calculated by $\chi=\Delta p/S$, where $\Delta p$ is the difference between the highest and lowest blood pressures.

Figure 5:
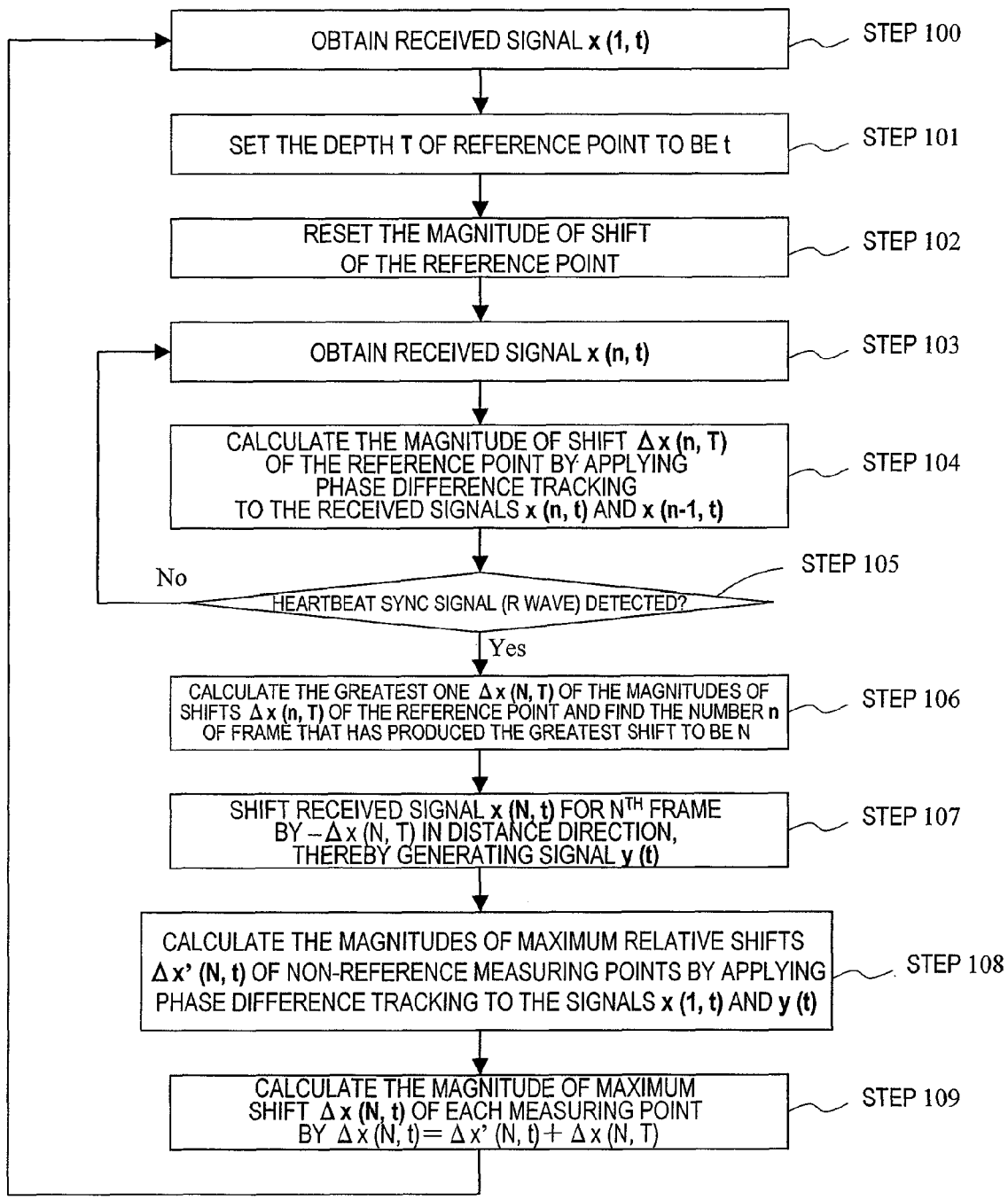
FIG. 5 is a flowchart showing the major processing steps of the measuring process of the first preferred embodiment.
Figure 6:
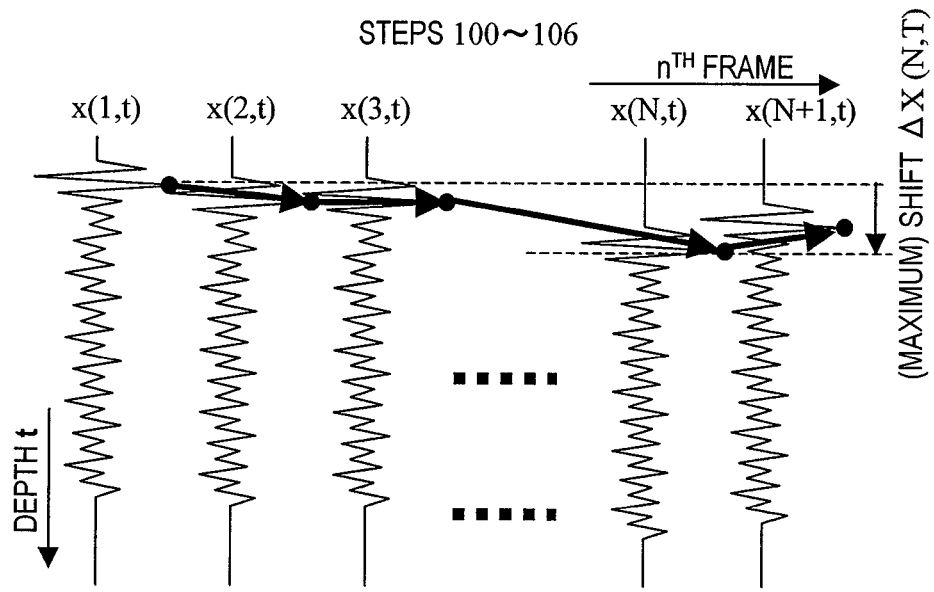
FIG. 6 shows how the processing should be performed in a major processing step of the measuring process of the first preferred embodiment.
Figure 7:
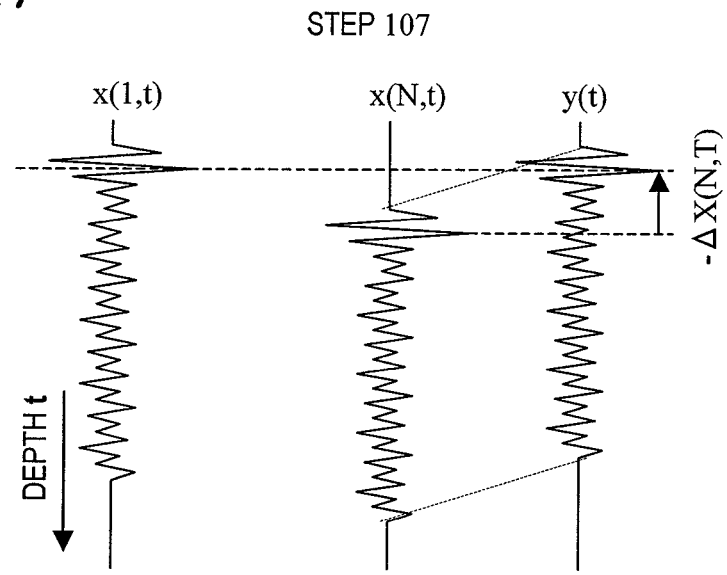
FIG. 7 shows how the processing should be performed in another major processing step of the measuring process of the first preferred embodiment.
Figure 8:
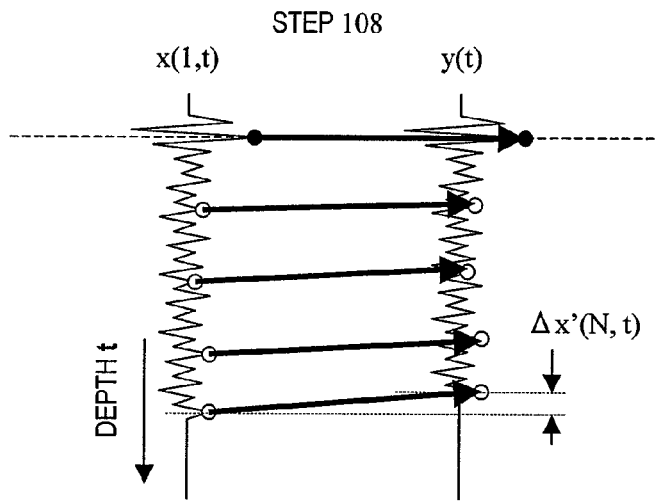
FIG. 8 shows how the processing should be performed in another major processing step of the measuring process of the first preferred embodiment.

Hereinafter, major processing steps of the measuring process according to this preferred embodiment will be described in detail with reference to FIGS. 3, 4 and FIGS. 5 through 8. FIG. 5 is a flowchart showing the major processing steps of the measuring process of this preferred embodiment. And FIGS. 6, 7 and 8 illustrate how the measuring process gets done in those major processing steps of this preferred embodiment.

First of all, the ultrasonic probe 13 is driven to send out an ultrasonic wave toward a target vital tissue and the ultrasonic wave reflected gets detected at the receiving section 15, thereby obtaining a received signal x (1, t) for the 1$^{st}$ frame in Step 100. FIG. 6 shows what waveforms received signals will have in a situation where ultrasonic waves are repeatedly transmitted toward the same site on the posterior wall of the arterial vascular wall. In FIG. 6, the received signal for an ultrasonic wave that has been transmitted for the first time is identified by x (1, t) and the received signal for an ultrasonic wave that has been transmitted for the second time is identified by x (2, t), where t is the reception time that has been counted from the transmission time and represents a depth. In the following description, a received signal for an ultrasonic wave that has been transmitted for the n$^{th}$ time will be referred to herein as a "received signal x (n, t) for the n$^{th}$ frame".

Next, the reference point setting section 51 sets the depth T of the reference point on the received signal for the 1$^{st}$ frame in Step 101. As described above, the reference point may be set either automatically or manually. In FIG. 6, a portion of each received signal with almost no waves represents a reflected wave component that has come from somewhere in the blood flow, while a portion with surging waves represents a reflected wave component that has come from the boundary between the blood flow and the intima. Also, another portion with a speckle wave under those surging waves represents a reflected wave component that has come from the vascular wall. According to this preferred embodiment, the reference point is set on the boundary between the blood flow and the intima for the reasons described above. That is why the reference point is located on a wave with the greatest amplitude of the received signal x (1, t) for the 1$^{st}$ frame as indicated by the solid circle ● in FIG. 6.

Subsequently, the magnitude of shift $\Delta x$ (1, T) of the reference point that has been set is reset into zero in Step 102. That is to say, as shown in FIG. 6, the magnitude of shift $\Delta x$ (1, T) of the reference point on the received signal x (1, t) for the 1$^{st}$ frame is reset into zero.

Thereafter, another ultrasonic wave is transmitted toward the vital tissue to obtain another received signal (i.e., a received signal x (2, t) for the 2$^{nd}$ frame) in Step 103, where n=2 in this case. Then, the magnitude of shift of the reference point is calculated by the phase difference tracking method between the received signals x (2, t) and x (1, t) for the 2$^{nd}$ and 1$^{st}$ frames, thereby determining the magnitude of shift of the reference point in the received signal for the 2$^{nd}$ frame. More specifically, the phase difference tracking method is applied between the received signals for the 1$^{st}$ and 2$^{nd}$ frames, thereby calculating the magnitude of shift $\Delta x$ (2, T) of the reference point in Step 104, where n=2 in this case.

Next, it is determined whether or not a heartbeat sync signal has been detected. The heartbeat sync signal is used as a trigger to reset the measuring count every cardiac cycle and may be either an R wave of an electrocardiogram or have been generated on the R wave. As described above, any other biomedical signal such as a phonocardiogram may also be used.

Unless the reference point shift measuring section 52 has detected the heartbeat sync signal (i.e., if the answer to the query of Step 105 is NO), the processing steps 103 and 104 are carried out repeatedly, thereby determining the magnitude of shift $\Delta x$ (n, T) of the reference point in the received signal for the n$^{th}$ frame.

On the other hand, if the reference point shift measuring section 52 has detected the heartbeat sync signal in Step 105, the section 52 finds not only the number N of the frame that has produced the greatest shift of the reference point but also the magnitude of that greatest shift $\Delta x$ (N, T) among the magnitudes of shifts of the reference point that have ever been measured. Then, the frame number and the magnitude of the greatest shift $\Delta x$ (N, T) thus obtained are supplied to the received signal adjusting section 53.

The received signal adjusting section 53 receives the frame number and the magnitude of the greatest shift Δx (N, T) and shifts the received signal x (N, t) for the $N^{th}$ frame by −Δx (N, T) in the depth direction, thereby generating a signal y (t) in Step 107. As a result of this processing step, a received signal y (t), of which the reference point is aligned with that of the received signal for the $N^{th}$ frame, is obtained as shown in FIG. 7.

The shape variation calculating section 54 receives at least the first received signal x (1, t) and the signal y (t) that has been obtained in the previous processing step 107 from the received signal adjusting section and calculates the magnitudes of the maximum shifts Δx' (N, t) of non-reference measuring points in Step 108 by applying the phase difference tracking method between the first signal x (1, t) and the signal y (t) that has been generated in Step 107 as shown in FIG. 8, where the non-reference measuring points are indicated by the open circles ○. The position of the reference point agrees between x (1, t) and y (t) and the magnitude of shift thereof is zero. The magnitudes of maximum shifts Δx' (N, t) to be calculated in this processing step are relative values with respect to the magnitude of the greatest shift of the reference point.

If the modulus of elasticity needs to be determined by calculating the strain between measuring points, then the difference between the magnitudes of maximum shifts Δx (N, t) of the respective measuring points that have been calculated in the previous processing step 108 becomes the greatest thickness difference Δh. Thus, the tissue characteristic value calculating section 55 may calculate the modulus of elasticity by receiving the greatest thickness difference Δh between the respective measuring points and using the information about the blood pressure provided by the blood pressure manometer 12.

Then, in Step 109, the magnitude of greatest shift Δx (N, T) of the reference point that has been obtained in Step 106 is added to the magnitude of maximum shift Δx' (N, t) that has just been calculated in the previous processing step 108. In this manner, the absolute value of the maximum shift Δx (N, t) of the non-reference measuring points can be calculated.

By performing these processing steps 100 through 108 or 109 a number of times, the modulus of elasticity can be measured consecutively every cardiac cycle.

As described above, the ultrasonic diagnostic apparatus of this preferred embodiment sets a reference point on a received signal and measures the magnitude of shift of that reference point, thereby estimating the magnitude of displacement of the overall vital tissue that is the object of measurement. And by shifting the received signal in the distance direction based on that magnitude of shift, the displacement of the overall vital tissue can be canceled. That is why by measuring a tiny movement of the vital tissue using such a shifted signal, the error that would have grown proportionally to the magnitude of displacement can be minimized and the magnitude of such a small displacement of the vital tissue can be measured with high accuracy. More particularly, the magnitude of the greatest shift of the reference point that has been set on the received signal is obtained every cardiac cycle. The received signal is shifted in the distance direction based on the magnitude of the greatest shift thus obtained. The received signal is adjusted such that the position of the reference point never changes in the distance direction. And the magnitudes of maximum relative shifts of respective measuring points are calculated based on the received signal adjusted, thereby obtaining the thickness difference, the magnitude of strain and the modulus of elasticity highly accurately while preventing the error from growing proportionally to the magnitude of shift.

Embodiment 2

Hereinafter, a second preferred embodiment of an ultrasonic diagnostic apparatus according to the present invention will be described. The apparatus of the first preferred embodiment described above can estimate the magnitude of the maximum strain of each measuring point in one cardiac cycle highly accurately. Meanwhile, according to this preferred embodiment, the shift of each measuring point can be estimated highly accurately within one cardiac cycle.

Figure 9:
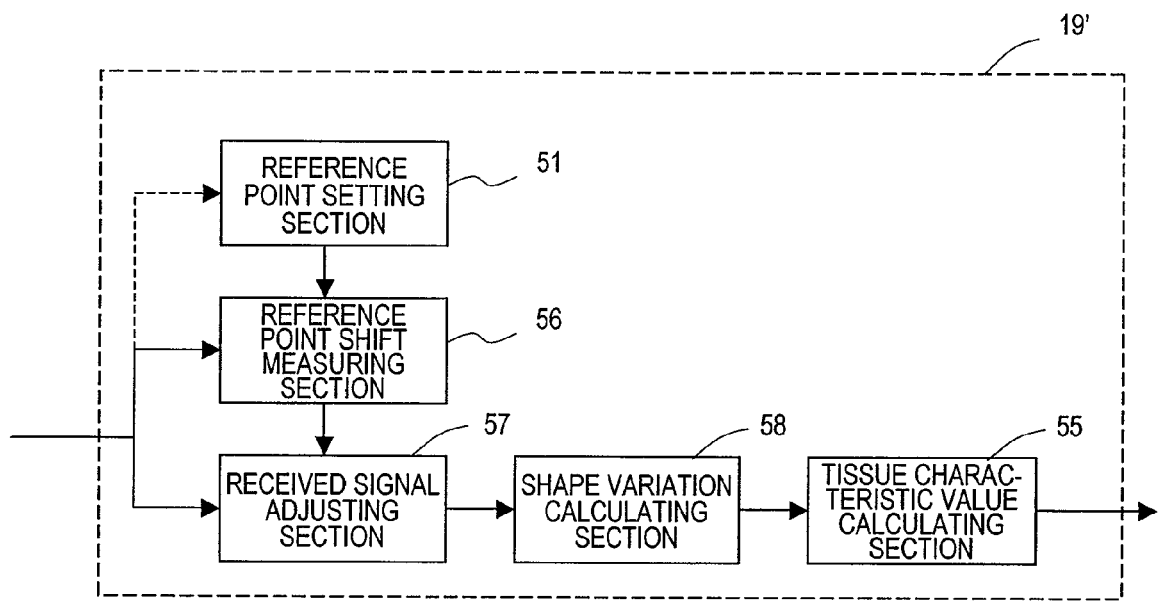
FIG. 9 is a block diagram illustrating a detailed configuration for a computing section for an ultrasonic diagnostic apparatus as a second preferred embodiment of the present invention.

FIG. 9 is a block diagram illustrating a configuration for a computing section 19' for the ultrasonic diagnostic apparatus of this preferred embodiment. Except this computing section 19', the apparatus of this second preferred embodiment has the same configuration as the counterpart of the first preferred embodiment shown in FIG. 3.

The computing section 19' includes the reference point setting section 51, a reference point shift measuring section 56, a received signal adjusting section 57, a shape variation calculating section 58 and a tissue characteristic value calculating section 55.

As in the first preferred embodiment described above, the reference point setting section 51 sets a reference point on the received signal in order to determine the magnitude of displacement of the overall vital tissue that is the object of measurement.

The reference point shift measuring section 56 measures the magnitude of shift of the reference point using the received signal for each frame. And if the magnitude of shift is at least an integral number of times (but not zero times) as much as a predetermined value, then the reference point shift measuring section 56 multiplies the predetermined value by the integer and outputs the product as the magnitude of shift to the received signal adjusting section 57.

The received signal adjusting section 57 receives the magnitude of shift, which has just been measured by the reference point shift measuring section 56, and adjusts the position of the reference point on the received signal. Specifically, the received signal adjusting section 57 generates a signal by shifting the received signal in the distance direction (i.e., along the axis) by the magnitude of shift obtained. As for a received signal, of which the absolute value of the shift is less than the predetermined value, however, the position of the reference point is not adjusted.

The shape variation calculating section 58 calculates the magnitudes of shifts of the multiple measuring points that have been set in the vital tissue based on the adjusted received signal. This calculation can be done by the phase difference tracking method disclosed in Patent Document No. 1. Specifically, by carrying out the phase difference tracking between the received signal for the $1^{st}$ frame and the received signal adjusted or between two adjusted received signals that are adjacent to each other on the time axis, the magnitudes of shifts at the respective measuring points are calculated. Furthermore, based on the magnitudes of shifts of the respective measuring points, the shape variation calculating section 58 also calculates the greatest thickness difference between two arbitrary points that have been set based on the multiple measuring points.

The tissue characteristic value calculating section 55 figures out the characteristic property value (e.g., the magnitude of strain in this preferred embodiment) of the tissue based on the greatest thickness difference. If the measuring points are arranged two-dimensionally within the measuring region, the magnitude of strain may be calculated between each pair of the measuring points. Then, the two-dimensional distribution of the magnitudes of strains within the measuring region can be obtained.

As in the first preferred embodiment described above, the image synthesizing section 21 synthesizes together the tomographic image that has been generated by the tomographic image generating section 24 and the two-dimensional map data of the magnitudes of strains that have been obtained by the computing section 19', and gets the resultant synthetic image presented on the display section 30.

Figure 10:
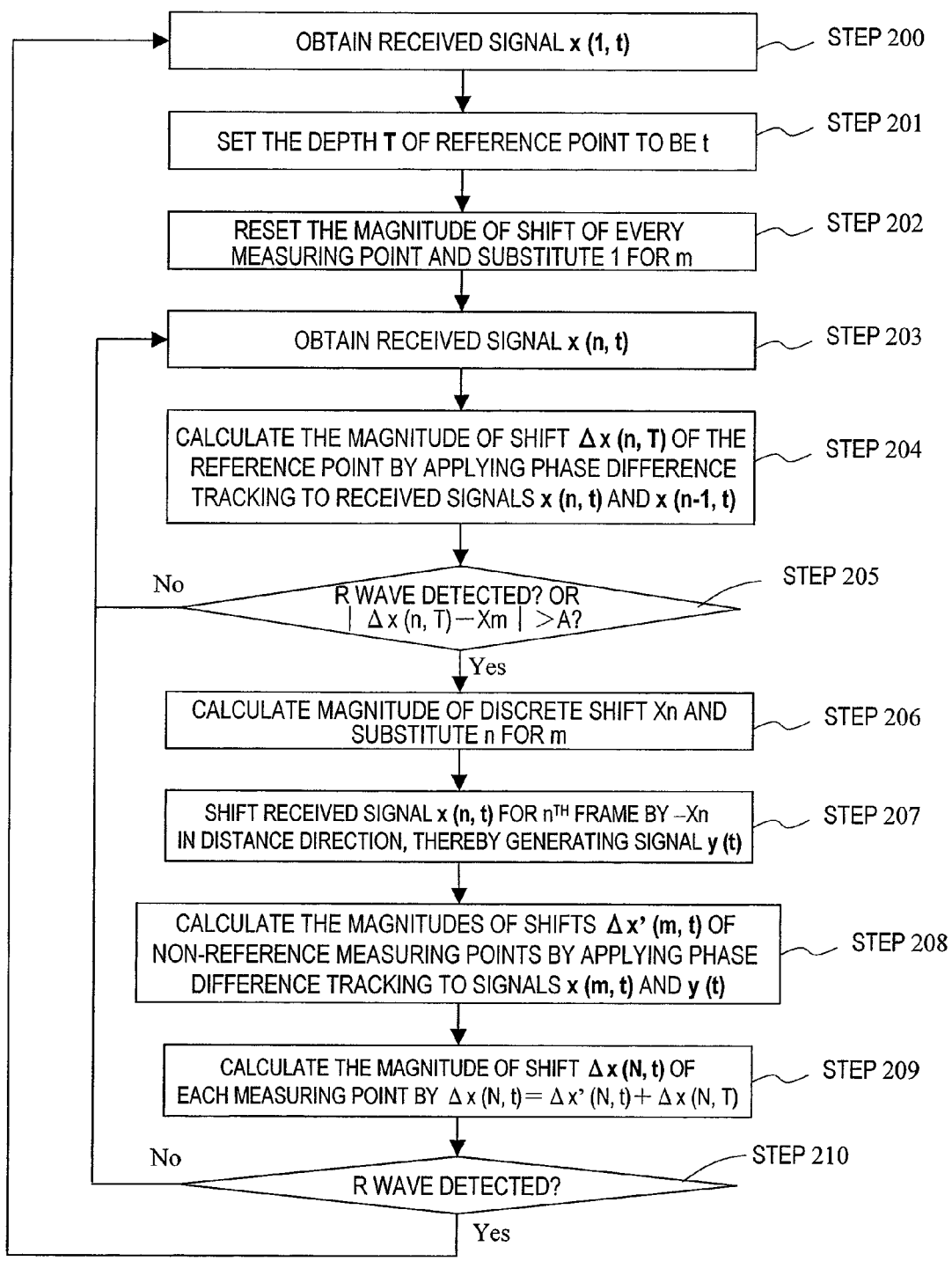
FIG. 10 is a flowchart showing the major processing steps of the measuring process of the second preferred embodiment.

Hereinafter, major processing steps of the measuring process according to this preferred embodiment will be described in detail with reference to FIGS. 3, 9 and FIGS. 10 through 14. FIG. 10 is a flowchart showing the major processing steps of the measuring process of this preferred embodiment. And FIGS. 11 through 14 illustrate how the measuring process gets done in those major processing steps of this preferred embodiment.

Figure 11:
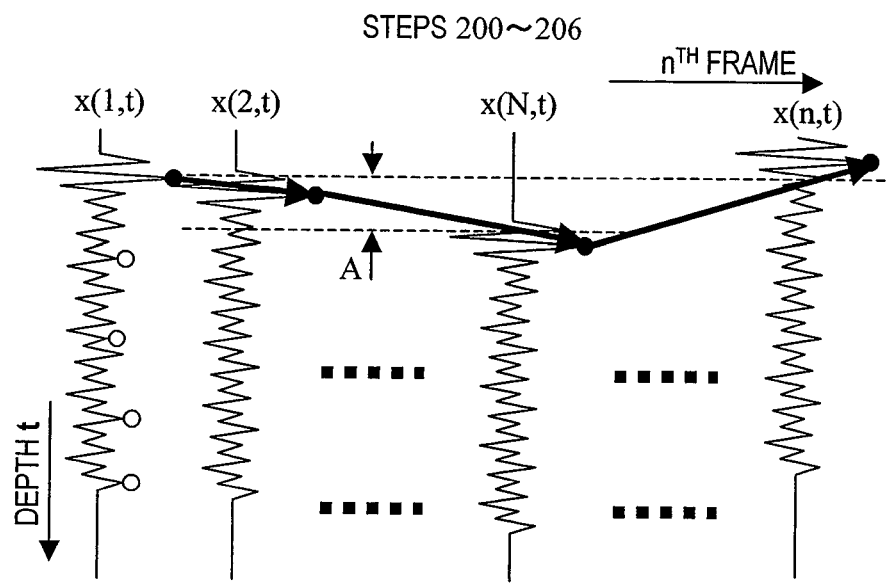
FIG. 11 shows how the processing should be performed in a major processing step of the measuring process of the second preferred embodiment.

First of all, the ultrasonic probe 13 is driven to send out an ultrasonic wave toward a target vital tissue and the ultrasonic wave reflected gets detected at the receiving section 15, thereby obtaining a received signal x (1, t) for the $1^{st}$ frame in Step 200. FIG. 11 shows what waveforms received signals have in a situation where ultrasonic waves are repeatedly transmitted toward the same site on the posterior wall of the arterial vascular wall. In FIG. 11, the received signal for an ultrasonic wave that has been transmitted for the first time is identified by x (1, t) and the received signal for an ultrasonic wave that has been transmitted for the second time is identified by x (2, t), where t is the reception time that has been counted from the transmission time and represents a depth. In the following description, a received signal for an ultrasonic wave that has been transmitted for the $n^{th}$ time will be referred to herein as a "received signal x (n, t) for the $n^{th}$ frame.

Next, as in the first preferred embodiment described above, the reference point setting section 51 sets the depth T of the reference point on the received signal for the $1^{st}$ frame in Step 201. The reference point is located on a wave with the greatest amplitude of the received signal x (1, t) for the $1^{st}$ frame as indicated by the solid circle ● in FIG. 11.

Subsequently, the magnitude of shift Δx (1, T) of the reference point that has been set is reset into zero in Step 202. That is to say, as shown in FIG. 11, the magnitude of shift Δx (1, T) of the reference point on the received signal x (1, t) for the $1^{st}$ frame is reset into zero. Also, "1" representing the $1^{st}$ frame is substituted for the variable m that indicates the frame just before the magnitudes of shifts of all measuring points have been determined (i.e., the last frame).

Thereafter, another ultrasonic wave is transmitted toward the vital tissue to obtain another received signal (i.e., a received signal x (2, t) for the $2^{nd}$ frame) in Step 203, where n=2 in this case. Then, the magnitude of shift of the reference point is calculated by the phase difference tracking method between the received signals x (2, t) and x (1, t) for the $2^{nd}$ and $1^{st}$ frames, thereby determining the magnitude of shift of the reference point in the received signal for the $2^{nd}$ frame. More specifically, the phase difference tracking method is applied between the received signals for the $1^{st}$ and $2^{nd}$ frames, thereby calculating the magnitude of shift Δx (2, T) of the reference point in Step 204, where n=2 in this case.

Next, it is determined whether or not a heartbeat sync signal has been detected. And it is also determined whether or not the absolute value of the difference between the position of a reference point for the $m^{th}$ frame, in which the magnitude of shift of every measuring point has been determined at last, and that of the reference point for the current received signal is equal to or greater than a predetermined value A in Step 205. As in the first preferred embodiment described above, the heartbeat sync signal may be an R wave of an electrocardiogram. Alternatively, a phonocardiogram may also be used or a sync signal may also be obtained by analyzing the waveform representing the shift of the reference point Δx (n, T).

The predetermined value A may be determined arbitrarily but is preferably a sampling interval of the received signal. If no heartbeat sync signal has been detected and if the absolute value of the difference between the position of a reference point for the $m^{th}$ frame, in which the magnitude of shift of every measuring point has been determined at last, and that of the reference point for the current received signal is less than the predetermined value A, then the processing steps 203 and 204 are carried out repeatedly, thereby determining the magnitude of shift Δx (n, T) of the reference point on the received signal for the $n^{th}$ frame.

On the other hand, if the heartbeat sync signal has been detected or if the absolute value of the difference between the positions of two reference points is equal to or greater than the predetermined value A, then a magnitude of shift that is an integral number of times (but not zero times) as great as A and that is closest to the magnitude of shift Δ x (n, T) of the reference point is obtained as the magnitude of discrete shift Xn in Step 206. Also, the frame number in this processing step is substituted for the number m of the frame in which the magnitude of shift of every measuring point has been determined.

Figure 12:
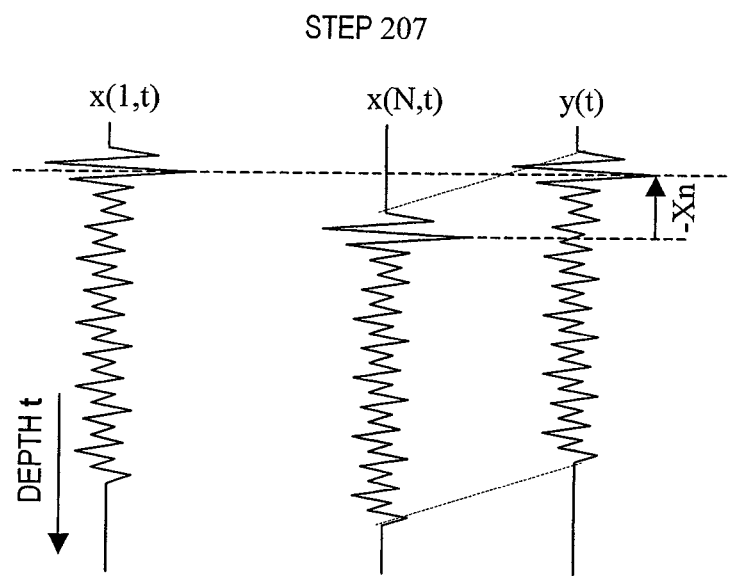
FIG. 12 shows how the processing should be performed in another major processing step of the measuring process of the second preferred embodiment.

Next, the received signal x (n, t) for the $n^{th}$ frame is shifted by −Xn in the depth direction, thereby generating a signal y (t). As a result, a received signal, of which the reference point is aligned with that of the received signal for the $n^{th}$ frame, is obtained in Step 207 as shown in FIG. 12.

Figure 13:
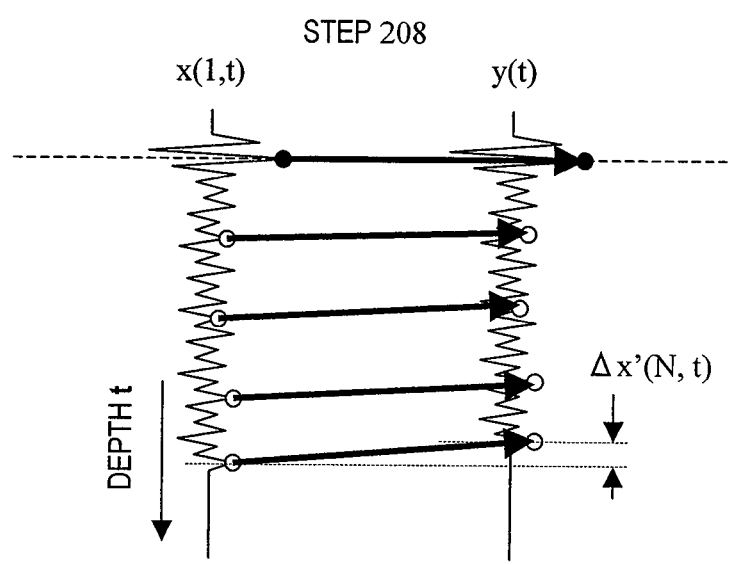
FIG. 13 shows how the processing should be performed in another major processing step of the measuring process of the second preferred embodiment.

Subsequently, in Step 208, the magnitudes of shifts Δx' (N, t) of non-reference measuring points are calculated by applying the phase difference tracking method between the signal x (m, t) for the previous frame in which the magnitude of shift of every measuring point has been determined and y (t) that has been obtained in Step 207 as shown in FIG. 13, where the non-reference measuring points are indicated by the open circles ○. The position of the reference point agrees between x (1, t) and y (t) and the magnitude of shift thereof is zero. The magnitudes of shifts Δx' (N, t) to be calculated in this processing step are relative values with respect to the reference point.

Then, the magnitude of shift Δx (n, T) that has been obtained in Step 204 is added to the magnitudes of shifts Δx' (N, t) of the non-reference points that have just been calculated in the previous processing step 208, thereby calculating the magnitudes of shifts Δx (N, t) of the non-reference measuring points.

Subsequently, it is determined in Step 209 whether or not the heartbeat sync signal has been detected. If the answer is NO, then the processing steps 203 through 209 are performed all over again. On the other hand, if the answer is YES, the measuring process for the current cardiac cycle is finished to start a measuring process for the next cardiac cycle. For that purpose, the processing steps 200 through 210 are performed all over again.

Figure 14:
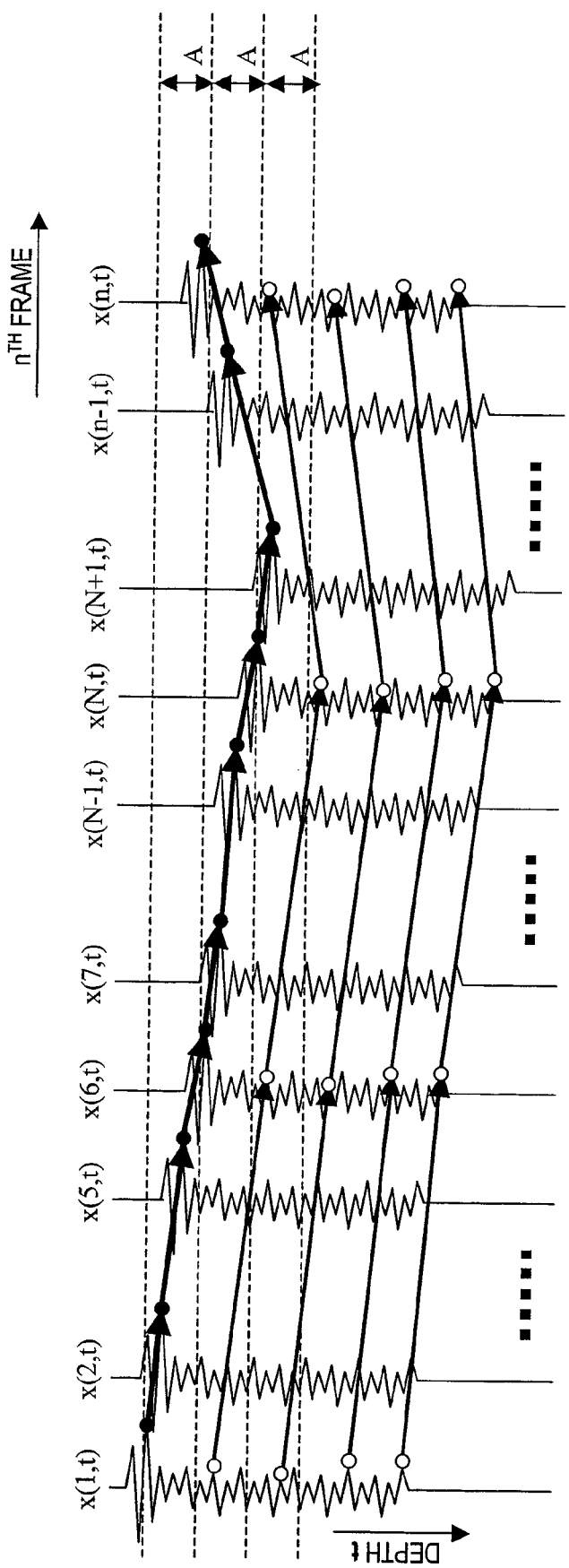
FIG. 14 shows how the processing should be performed in another major processing step of the measuring process of the second preferred embodiment.

FIG. 14 shows the results obtained by tracking the shifts of the respective measuring points as described above. As can be seen from these results, the cumulative error to be inevitably caused by the phase difference tracking method can be reduced and the tracking accuracy can be improved. As shown in FIG. 14, when the magnitude of shift of the reference point exceeds the predetermined value A, the received signal is shifted to obtain the magnitude of shift of the measuring point. This magnitude of shift is calculated by the phase difference tracking method with the magnitude of displacement of the overall vital tissue subtracted, and therefore, the error to be proportional to the magnitude of shift has decreased. That is why the measuring point can be tracked with higher accuracy. On top of that, the magnitude of shift can be calculated a number of times during one cardiac cycle, thus increasing the time resolution of the measuring process as well.

Optionally, this preferred embodiment may be combined with the first preferred embodiment. In that case, a single reference point may also be set but the reference point shift measuring section does not have to measure the magnitude of the greatest shift of the reference point and the magnitude of shift for each frame independently of each other.

In the preferred embodiment described above, the received signal for the previous (or last) frame in which the magnitude of shift of a measuring point has just been obtained is used as a reference for determining the magnitude of shift of that measuring point in each cardiac cycle. Specifically, if the magnitude of shift from the previous frame in which the magnitude of shift of each measuring point has just been measured becomes equal to or greater than a predetermined value A, the received signal is shifted an integral number of times as much as the predetermined value A, thereby determining the magnitude of shift from the previous frame, in which the magnitude of shift of each measuring point has just been measured, by the phase difference tracking method. However, the received signal for the first frame may also be used as a reference for determining the magnitude of shift of a measuring point in each cardiac cycle. Specifically, in that case, if the magnitude of shift from the first frame becomes equal to or greater than an integral number of times as much as the predetermined value A, the received signal may be shifted the integral number of times as much as the predetermined value A, thereby determining the magnitude of shift from the first frame by the phase difference tracking method.

Experimental Example

To confirm the effect of the present invention, the magnitude of strain of an elastic tube was measured with the ultrasonic diagnostic apparatus of the first preferred embodiment described above. As samples for measurements, a tube of silicone rubber with an outside diameter of 10 mm and an inside diameter of 8 mm (which will be referred to herein as Sample A) and a double tube consisting of an inner tube of silicone rubber with an outside diameter of 10 mm and an inside diameter of 8 mm and an outer tube of silicone rubber with an outside diameter of 12 mm and an inside diameter of 10 mm (which will be referred to herein as "Sample B") were provided. In the Sample B tube, the inner tube had a smaller modulus of elasticity than the outer tube.

The liquid in these samples was periodically pressurized with a fluid pump to contract the samples periodically and make measurements using the ultrasonic diagnostic apparatus of the first preferred embodiment. Also, for the purpose of comparison, the magnitudes of strains of the same two samples were measured by a conventional ultrasonic diagnostic apparatus using the ordinary phase difference tracking method.

Figure 15A:
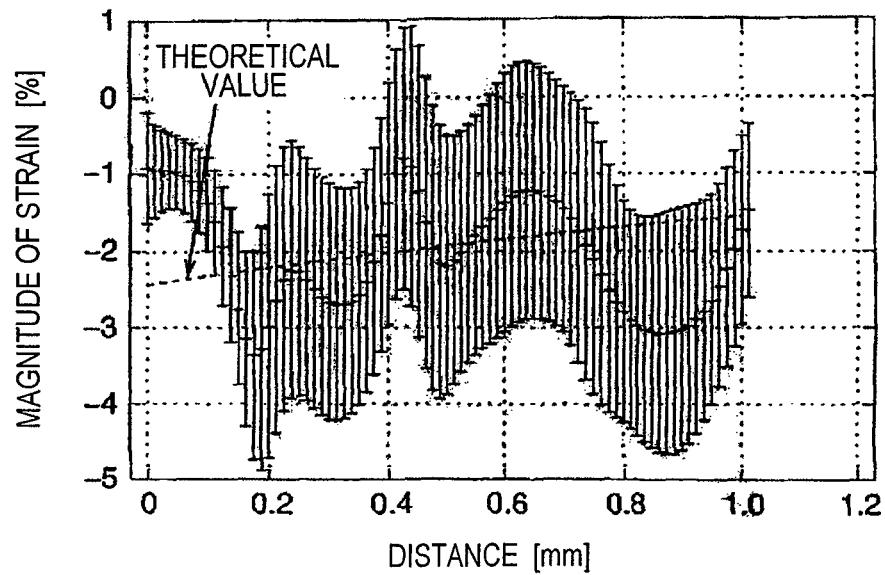
FIG. 15A shows the result of a measurement that was carried out on a sample using a conventional ultrasonic diagnostic apparatus.
Figure 15B:
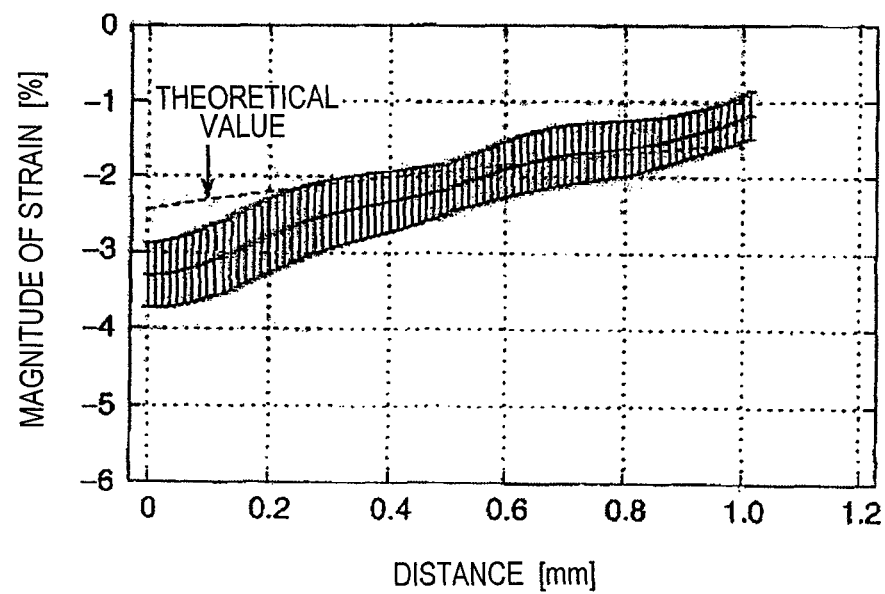
FIG. 15B shows the result of a measurement that was carried out on a sample using an ultrasonic diagnostic apparatus according to the present invention.

FIGS. 15A and 15B show the results of measurements that were carried out on Sample A using the conventional ultrasonic diagnostic apparatus and the ultrasonic diagnostic apparatus of the present invention, respectively. In FIGS. 15A and 15B, the abscissa represents the distance in the radial direction of the tube while the ordinate represents the magnitude of strain. The value of the magnitude of strain is also indicated by an error bar. And the dashed curve represents the radial distribution of magnitudes of theoretical strains that were calculated based on the modulus of elasticity of the silicone rubber that was used as a material for the tube.

When the conventional ultrasonic diagnostic apparatus was used, the average of the magnitudes of strains calculated in the radial direction was roughly close to the theoretical value as shown in FIG. 15A. But their distribution was quite non-uniform. On the other hand, when the ultrasonic diagnostic apparatus of the present invention was used, the average closely agreed with the theoretical value and the degree of non-uniformity could also be reduced significantly.

Figure 16A:
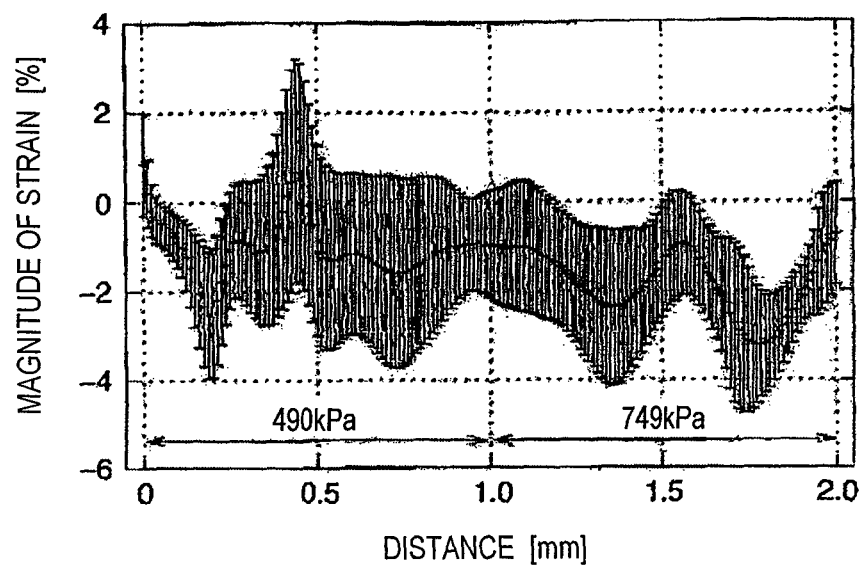
FIG. 16A shows the result of a measurement that was carried out on another sample using the conventional ultrasonic diagnostic apparatus.
Figure 16B:
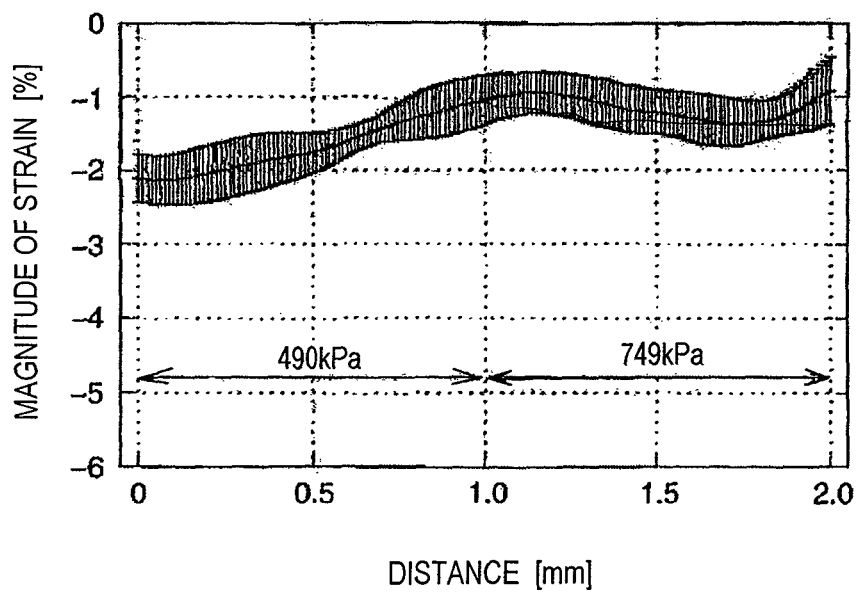
FIG. 16B shows the result of a measurement that was carried out on another sample using the ultrasonic diagnostic apparatus of the present invention.

FIGS. 16A and 16B show the results of measurements that were carried out on Sample B using the conventional ultrasonic diagnostic apparatus and the ultrasonic diagnostic apparatus of the present invention, respectively. Sample B was made up of two tubes with mutually different hardness values. When the measuring process was carried out with the conventional ultrasonic diagnostic apparatus, however, the difference in the magnitude of strain corresponding to the difference in hardness could not be sensed clearly as shown in FIG. 16A. On the other hand, when the ultrasonic diagnostic apparatus of the present invention was used, the magnitude of strain of the softer inner tube was found greater than that of the harder outer tube as shown in FIG. 16B. As a result, the difference in the magnitude of strain corresponding to the difference in hardness could be seen clearly.

As can be seen from these results, the ultrasonic diagnostic apparatus of the present invention can measure the magnitude of strain with high accuracy. Among other things, even if there is a region with a different modulus of elasticity within the measuring region, the difference in the magnitude of strain corresponding to the difference in the modulus of elasticity can be sensed properly. That is why if the magnitude of strain or the modulus of elasticity of the arterial vascular wall of an organism is measured with the ultrasonic diagnostic apparatus of the present invention, then a region with a distinct modulus of elasticity, produced by some sort of lesion, should be able to be located accurately. As a result, an ultrasonic diagnostic apparatus that allows the doctor to make a proper diagnosis on a characteristic property of a vital tissue is realized.

INDUSTRIAL APPLICABILITY

The present invention is effectively applicable to an ultrasonic diagnostic apparatus for evaluating the characteristic properties of a given vital tissue and is applicable particularly effectively to an ultrasonic diagnostic apparatus for evaluating the elastic property of a vascular wall.

The invention claimed is:

1. An ultrasonic diagnostic apparatus comprising:
 a transmitting section configured to drive an ultrasonic probe that sends out first and second ultrasonic transmitted waves toward a vital tissue;
 a receiving section configured to amplify ultrasonic reflected waves, produced by getting the first and second ultrasonic transmitted waves reflected by the vital tissue and then received at the ultrasonic probe, to generate first and second received signals which correspond to the first and second ultrasonic transmitted waves, respectively;
 a reference point shift measuring section configured to measure the magnitude of shift of a reference point that has been set on the first received signal, the magnitude of shift of the reference point being measured between the first and second received signals along a distance direction;

a received signal adjusting section configured to generate a third received signal by adjusting the position of the second received signal in a distance direction according to the magnitude of shift of the reference point such that the reference point in the third received signal is located at the same depth in the vital tissue as set in the first received signal; and a shape variation calculating section configured to determine magnitudes of positional displacements at multiple measuring points that have been set in the vital tissue, wherein the positional displacements are displacements of the measuring points between the first received signal and the third received signal.

2. The ultrasonic diagnostic apparatus of claim 1, wherein the vital tissue makes a movement in a cycle time corresponding to one cardiac cycle, and wherein the reference point shift measuring section determines the magnitude of the greatest shift of the reference point within one cardiac cycle.

3. The ultrasonic diagnostic apparatus of claim 2, wherein the transmitting section and the receiving section send and receive the first and second ultrasonic transmitted waves a number of times every cardiac cycle so as to scan a measuring region that has been defined in the vital tissue, thereby generating first and second received signals for multiple frames, and wherein the received signal adjusting section adjusts the position of the second received signal in the distance direction to generate the third received signal at least in a frame in which the reference point has the greatest magnitude of shift in each said cardiac cycle.

4. The ultrasonic diagnostic apparatus of claim 3, wherein the received signal adjusting section adjusts the position of the second received signal in the distance direction to generate the third received signal in the frame in which the reference point has the greatest magnitude of shift such that the positions of the reference point are aligned with each other in the distance direction.

5. An ultrasonic diagnostic apparatus comprising:

a transmitting section configured to drive an ultrasonic probe that sends out first and second ultrasonic transmitted waves toward a vital tissue such that the first and second ultrasonic transmitted waves are sent at each of multiple frames for a tomographic image;

a receiving section configured to amplify ultrasonic reflected waves, produced by getting the first and second ultrasonic transmitted waves reflected by the vital tissue and then received at the ultrasonic probe, to generate first and second received signals which correspond to the first and second ultrasonic transmitted waves, respectively;

a reference point shift measuring section configured to measure the magnitude of shift of a reference point that has been set on the first received signal, the magnitude of shift of the reference point being measured between the first and second received signals along a distance direction;

a received signal adjusting section configured to generate a third received signal by adjusting the position of the second received signal in a distance direction according to the magnitude of shift of the reference point; and a shape variation calculating section configured to determine the magnitudes of positional displacements at multiple measuring points that have been set in the vital tissue based on the adjusted received signal, wherein the reference point shift measuring section measures the magnitude of shift of the reference point every frame, and if the magnitude of shift is an integral number of times (but not zero times) as much as a predetermined value or greater, then the reference point shift measuring section multiplies the predetermined value by the integer and outputs the product as the magnitude of shift to the received signal adjusting section, and wherein the received signal adjusting section generates the third received signal by shifting the position of the second received signal in the distance direction by the magnitude of shift.

6. The ultrasonic diagnostic apparatus of claim 5, wherein the received signal adjusting section adjusts the position of the second received signal in the distance direction to generate the third received signal so as to cancel the magnitude of shift.

7. The ultrasonic diagnostic apparatus of claim 6, wherein the predetermined value is equal to a sampling interval.

8. The ultrasonic diagnostic apparatus of claim 1, wherein the vital tissue is an arterial vascular wall, and wherein the reference point is set at a point on the received signal that corresponds to the boundary between a vascular lumen and an intima.

9. The ultrasonic diagnostic apparatus of claim 1, wherein the vital tissue makes a movement in a cycle time corresponding to one cardiac cycle, and wherein the shape variation calculating section calculates the greatest thickness difference between two arbitrary points that have been set based on the multiple measuring points according to the magnitudes of positional displacements.

10. The ultrasonic diagnostic apparatus of claim 9, further comprising a tissue characteristic value calculating section configured to calculate a characteristic property value of the tissue based on the greatest thickness difference.

11. The ultrasonic diagnostic apparatus of claim 10, wherein the vital tissue is an artery and wherein the characteristic property value is a modulus of elasticity.

12. The ultrasonic diagnostic apparatus of claim 1, wherein the reference point shift measuring section determines the magnitude of shift by analyzing the phase at the reference point of the first and second received signals.

13. The ultrasonic diagnostic apparatus of claim 1, wherein the shape variation calculating section calculates the magnitudes of positional displacements by analyzing the phases at the respective measuring points of the third received signal.

* * * * *